(12) United States Patent
Mori

(10) Patent No.: US 6,294,576 B1
(45) Date of Patent: Sep. 25, 2001

(54) PYRETHROID COMPOUNDS AND COMPOSITION FOR CONTROLLING PEST CONTAINING THE SAME

(75) Inventor: Tatsuya Mori, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/418,606

(22) Filed: Oct. 15, 1999

(30) Foreign Application Priority Data

Nov. 20, 1998 (JP) .................................................. 10-330980
Apr. 26, 1999 (JP) .................................................. 11-118003

(51) Int. Cl.[7] .................................................... A01N 53/02
(52) U.S. Cl. ........................... 514/531; 424/405; 424/409
(58) Field of Search ............................ 514/531; 424/405, 424/409

(56) References Cited

FOREIGN PATENT DOCUMENTS

| | | |
|---|---|---|
| 0054360 | 6/1982 | (EP) . |
| 0302612 | 2/1989 | (EP) . |
| 0381563 | 8/1990 | (EP) . |
| 0926129 | 6/1999 | (EP) . |
| 0939073 | 9/1999 | (EP) . |

*Primary Examiner*—Neil S. Levy
(74) *Attorney, Agent, or Firm*—Stevens, Davis, Miller & Mosher, LLP

(57) ABSTRACT

The composition for controlling pest of the present invention contains 4-methoxymethyl-2,3,5,6-tetrafluorobenzyl 3-(2-methyl-1-propenyl)-2,2-dimethyl-cyclopropanecarboxylate represented by the formula:

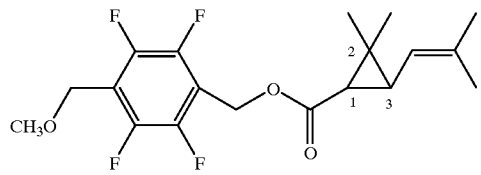

as an active ingredient.

5 Claims, No Drawings

PYRETHROID COMPOUNDS AND COMPOSITION FOR CONTROLLING PEST CONTAINING THE SAME

The present invention relates to a pyrethroid compound and a composition for controlling pest which contains said compound as an active ingredient.

It has been known that some pyrethroid compounds containing an alcohol moiety derived from a certain fluorine-substituted benzyl alcohol exhibit an insecticidal activity (EP-A-54360). These compounds, however, are not always sufficient in practical pest-controlling effect as an active ingredient of compositions for controlling pest.

In order to find a pyrethroid compound having a practically pest-controlling effect, the present inventors earnestly investigated and consequently found that 4-methoxymethyl-2,3,5,6-tetrafluorobenzyl 3-(2-methyl-1-propenyl)-2,2-dimethylcyclopropanecarboxylate represented by the formula shown below has an excellent pest-controlling effect and is very effective particularly in preventing domestic epidemics, whereby the present invention has been accomplished.

Thus, the present invention relates to 4-methoxymethyl-2,3,5,6-tetrafluorobenzyl 3-(2-methyl-1-propenyl)-2,2-dimethylcyclopropanecarboxylate (hereinafter referred to as the present compound) represented by the formula:

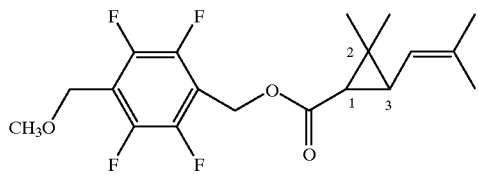

and a composition for controlling pest which contains the present compound as an active ingredient.

The present compound has stereoisomers relative to the asymmetric carbon atom on the cyclopropane ring and includes any active one of these stereoisomers and mixtures thereof.

In the present compound, (1R)-isomer or (1R)-enriched isomers are preferable in view of the excellent pesticidal activity. Moreover, (1R)-trans-isomer or (1R)-trans-enriched isomers are particularly preferable for controlling pests for preventing domestic epidemics.

The present compound can be produced, for example, by reacting an alcohol compound represented by the formula:

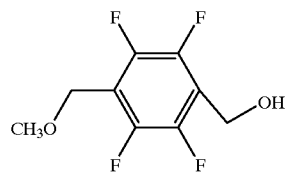

with a carboxylic acid compound represented by the formula:

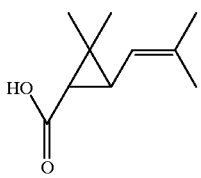

or a reactive derivative (e.g., acid halide or acid anhydride) of said carboxylic acid compound.

The reaction is usually carried out in a solvent in the presence of a condensing agent or a base.

The condensing agent includes, for example, dicyclohexylcarbodiimide and 1-(3-dimethylaminopropyl)-3-ethylcarbodiimide hydrochloride.

The base includes, for example, organic bases such as triethylamine, pyridine, N,N-diethylaniline, 4-dimethylaminopyridine and diisopropylethylamine.

The solvent includes, for example, hydro-carbons such as benzene, toluene and hexane; ethers such as diethyl ether and tetrahydrofuran; and halogenated hydrocarbons such as dichloromethane, 1,2-dichloroethane and chlorobenzene.

The reaction time ranges usually from 5 minutes to 72 hours.

The reaction temperature ranges usually from −20° C. to +100° C. (or from −20° C. to the boiling point of the solvent in the case where the boiling point of the solvent is lower than +100° C.), preferably from −5° C. to +100° C. (or from −5° C. to the boiling point of the solvent in the case where the boiling point of the solvent is lower than +100° C.).

Although the molar ratio of the alcohol compound to the carboxylic acid compound or its reactive derivative can be selected without any limitation, it is preferable to carry out the reaction by using them in an approximate molar ratio of 1:1.

The condensing agent or the base can be used in any amount of usually 1 mole or more, preferably 1 mole to 5 moles, per mole of said alcohol compound. The condensing agent or the base is appropriately chosen depending on the kind of said carboxylic acid compound or its reactive derivative to be reacted.

After completion of the reaction, the reaction solution is poured into water and then subjected to conventional work-up procedures such as extraction with an organic solvent, concentration and the like to obtain the present compound. Also, the present compound can be purified by operations such as chromatography, distillation and the like.

The above-mentioned alcohol compound and carboxylic acid compound can be produced according to, for example, the process disclosed in EP-A-54360.

Specific examples of the pests on which the present compound has a controlling effect are the following arthropods:

Lepidoptera

Pyralidae (pyralid moths) such as *Chilo suppressalis* (rice stem borer), *Cnaphalocrocis medinalis* (rice leafroller) and *Plodia interpunctella* (Indian meal moth); Noctuidae such as *Spodoptera litura* (tobacco cutworm), *Pseudaletia separata* (rice armyworm) and *Mamestra brassicae* (cabbage armyworm); Pieridae such as *Pieris rapae crucivora* (common cabbageworm); Tortricidae (tortricid moths) such as Adoxophyes spp.; Carposinidae; Lyonetiidae (lyonetiid moths); Lymantriidae (tussock moths); Antographa spp.;

Agrotis spp. such as *Agrothis segetum* (turnip cutworm) *and Agrothis ipsilon* (black cutworm); Helicoverpa spp.; Heliothis pps.; *Plutella xylostella* (diamondback moth); *Parnara guttata* (rice skipper); *Tinea pellionella* (casemaking clothes moth); *Tineola bisselliella* (webbing clothes moth); etc.

Diptera

*Culex* spp. such as *Culex pipiens pallens* (common mosquito)and *Culex tritaeniorhynchus;* Aedes spp. such as *Aedes aegypti* and *Aedes albopictus;* Anopheles spp. such as *Anopheles sinensis;* Chironomidae (midges); Muscidae such as Musca domestica (housefly), *Muscina stabulans* (false stablefly) and *Fannia canicularis* (little housefly); Calliphoridae; Sarcophagidae; Anthomyiidae (anthomylid flies) such as *Delia platura* (seedcorn maggot) and *Delia antiqua* (onion maggot); Tephritidae (fruit flies); Drosophilidae (small fruit flies, vinegar flies); Psychodidae (moth flies, sand flies); Phoridae; Simuliidae (black flies); Tabanidae; Stomoxyidae (stable flies); biting midges; etc.

Dictyoptera

*Blattella germanica* (German cockroach), *Periplaneta fuliginosa* (smokybrown cockroach), *Periplaneta americana* (American cockroach), *Periplaneta brunnea* (brown cockroach), *Blatta orientalis* (oriental cockroach), etc.

Hymenoptera

Formicidae (ants); Vespidae (hornets); Bethylidae (bethylid wasps); Tenthredinidae (sawflies) such as *Athalia rosae ruficornis* (cabbage sawfly); etc.

Siphonaptera

*Ctenocephalides canis, Ctenocephalides felis, Pulex irritans,* etc.

Anoplura

*Pediculus humanus, Phthirus pubis, Pediculus humanus* var. *capitis, Pediculus humanus* var. *corporis,* etc.

Isoptera termites

*Reticulitermes speratus, Coptotermes formosanus* (Formosan subterranean termite), etc.

Hemiptera

Delphacidae (planthoppers) such as *Laodelphax striatellus* (small brown planthopper), *Nilaparvata lugens* (brown planthopper) and *Sogatella furcifera* (white-backed rice planthopper); Deltocephalidae (leaf-hoppers) such as *Nephotettix cincticeps* (green rice leafhopper) and *Nephotetti virescens* (green rice leafhopper); Aphididae (aphids); Pentatomidae (bugs); Aleyrodidae (whiteflies); Coccidae (scales); Tingidae (lace bugs); Psyllidae (psyllids); etc.

Coleoptera

*Attagenus unicolor; Anthrenus verbasci* (varied carpet beetle); corn rootworms such as *Diabrotica virgifera* (western corn rootworm) and *Diabrotica undecimpunctaca howardi* (southern corn rootworm); Scarabaeidae (scarabs) such as *Anomala cuprea* (cupreous chafer) and *Anomala rufocuprea* (soybean beatle); Curculionidae (weevils) such as *Sitophilus zeamais* (maize weevil), *Lissorhoptrus oryzophilus* (ricewater weevil), *Anthonomus grandis grandis* (boll weevil) and *Callosobruchus chinensis* (adzuki bean weevil); Tenebrionidae (darkling beetles) such as *Tenebrio molitor* (yellow mealworm) and *Tribolium castaneum* (red fluor beetle); Chrysomelidae (corn rootworms) such as *Oulema oryzae* (rice leaf beetle), *Phyllotreta striolata* (striped flea beetles) and *Aulacophora femoralis* (cucurbit leaf beetle); Anobiidae; Epilachna spp. such as *Henosepilachna vigintioctopunctata* (twenty-eight-spotted ladybirds); Lyctidae (powder post beetles); Bostrychidae (false powder post beetles); Cerambycidae; *Paederus fuscipes* (robe beetle); etc.

Thysanoptera (thrips)

*Thrips palmi, Frankliniella occidentalis* (western flower thrips), Thrips *hawaiiensis* (flower thrips), etc.

Orthoptera

Gryllotalpidae (mole crickets), Acrididae (grasshoppers), etc.

Acarina (mites and ticks)

Pyroglyphidae such as *Dermatophagoides farinae* and *Dermatophagoides pteronyssinus;* Acaridae such as *Tyrophagus putrescentiae* Schrank (mold mite, copra mite, forage mite) and *Aleuroglyphus ovatus* Troupeau (brown legged grain mite); Glycyphagidae such as *Glycyphagus privatus, Glycyphagus domesticus* and *Glycyphagus destructor* Schrank (groceries mite); Cheyletidae such as *Cheyletus melaccensis* and *Cheyletus moorei;* Tarsonemidae; Chrtoglyphus; Oribatei; Tetranychidae (spider mites) such as *Tetranychus urticae* (two-spotted spider mite), *Tetranychus kanzawai* (Kanzawa spider mite), *Panonychus citri* (citrus red mite) and *Panonychus ulmi* (European red mite); Ixodidae such as *Haemaphysalis longicornis;* etc.

The present compound is markedly effective against Diptera such as Culex spp. (e.g., *Culex pipiens pallens* and *Culex tritaeniorhynchus*), Aedes spp. (e.g., *Aedes aegypti* and *Aedes albopictus*), Anopheles spp. (e.g., *Anopheles sinensis*), Muscidae (e.g., *Musca domestica, Muscina stabulans* and *Fannia Canicularis*), Calliphoridae, Sarcophagidae, Psychodidae, Phoridae, etc.; and Dictyoptera such as *Blattella germanica, Periplaneta fuliginosa, Periplaneta americana, Periplaneta brunnea, Blatta orientalis,* etc. Therefore, the present compound is especially effective as an active ingredient of a composition for controlling pest for preventing domestic epidemics.

When the present compound is used as an active ingredient of the composition for controlling pest, it is applied usually after having been formulated into various formulations, for example, oil formulations; emulsifiable concentrates; wettable powders; flowable concentrates (e.g., aqueous suspension concentrates and aqueous emulsion concentrates); granules; dusts; aerosols; heating fumigants (e.g., insecticidal coils, electric insecticidal mats, and solutions for heating fumigation using an absorbent wick); heating smoking formulations (e.g., self-burning-type smoking formulations, chemical-reaction-type smoking formulations, and electrically heating-type smoking formulations using a porous ceramic plate); non-heating volatile formulations (e.g., resin volatile formulations, and impregnated paper volatile formulations); foggings; ULV formulations; poisonous baits; or the like, either by mixing the present compound or a solution thereof with a solid carrier, liquid carrier, gaseous carrier base material for poisonous bait, or base material for insecticidal coil, and optionally adding auxiliaries for formulation such as surfactants, or by impregnating a base material such as an insecticidal coil or mat with the present compound or a solution thereof, and optionally adding a surfactant or other auxiliaries for formulation.

The present compound is particularly effective as an active ingredient of the above-mentioned heating fumigants such as insecticidal coils, electric insecticidal mats and solutions for heating fumigation using an absorbent wick.

These formulations usually contain the present compound as an active ingredient in an amount of 0.001 to 95% by weight.

The solid carrier used for formulation includes, for example, fine powders and granules of clays (e.g., kaolin clay, diatomaceous earth, synthetic hydrated silicon dioxide, bentonite, fubasami clay and acid clay), talcs, ceramics, and other inorganic minerals (e.g. sericite, quartz, activated carbon, calcium carbonate and hydrated silica). The liquid carrier includes, for example, water, alcohols (e.g., methanol and ethanol), ketones (e.g., acetone and methyl ethyl ketone), aromatic hydrocarbons (e.g., benzene, toluene, xylene, ethylbenzene and methylnaphthalene), aliphatic hydrocarbons (e.g., hexane, cyclohexane, kerosene and light oil), esters (e.g., ethyl acetate and butyl acetate), nitriles (e.g., acetonitrile and isobutyronitrile), ethers (e.g., diisopropyl ether and dioxane), acid amides (e.g., N,N-dimethylformamide and N,N-dimethylacetamide), halogenated hydrocarbons (e.g., dichloromethane, trichloroethane and carbon tetrachloride), dimethyl sulfoxide, and vegetable oils (e.g., soybean oil and cotton seed oil). The gaseous carrier, so-called propellant, includes for example, CFC gas, butane gas, LPG (liquefied petroleum gas), dimethyl ether and carbon dioxide.

The surfactant includes, for example, alkyl sulfates, alkylsulfonates, alkylarylsulfonates, alkyl aryl ethers and their polyoxyethylenated products, polyethylene glycol ethers, polyhydric alcohol esters and sugar alcohol derivatives.

The auxiliaries for formulation such as adhesive agents and dispersants include, for example, casein, gelatin, polysaccharides (e.g., starch powder, gum arabic, cellulose derivatives and alginic acid), lignin derivatives, bentonite, saccharides, and synthetic water-soluble polymers [e.g., poly-(vinyl alcohol)s, poly(vinyl pyrrolidone)s and poly (acrylic acid)s]. The stabilizer includes, for example, PAP (acidic isoproyl phospate), BHT (2,6-di-tert-butyl-4-methylphenol), BHA (a mixture of 2-tert-butyl-4-methoxyphenol and 3-tert-butyl-4-methoxyphenol), vegetable oils, mineral oils, surfactants, and fatty acids or their esters.

Base materials for the insecticidal coils include, for example, mixtures of vegetable powders (e.g., wood powder and Pyrethrum marc), charcoals and binders (e.g., Tabu powder, starch and gluten).

Base materials for electric insecticidal mats include, for example, plates obtained by coagulating fibrils of cotton linter or a mixture of cotton linter and pulp.

Base materials for self-burning-type smoking formulations include, for example, combustible and heat-generating agents (e.g., nitrates, nitrites, guanidine salts, potassium chlorate, nitrocellulose, ethyl-cellulose and wood powder), pyrolysis-promoting agents (e.g., alkali metal salts, alkaline earth metal salts, dichromates and chromates), oxygen-supplying agents (e.g., potassium nitrate), combustion-supporting agents (melamine and wheat starch), extending agents (e.g., diatomaceous earth) and binders (e.g., synthetic pastes).

Base materials for the chemical-reaction-type smoking formulations include, for example, heat-generating agents (e.g., sulfides, polysulfides, hydrosulfides and hydrate salts of alkali metals, and calcium oxide), catalysts (e.g., carbonaceous substances, iron carbide and activated clay), organic foaming agents (e.g., azodicarbonamide, benzenesulfonylhydrazide, dinitrosopentamethylenetetramine, polystyrenes and polyurethanes) and fillers (e.g., natural fiber pieces and synthetic fiber pieces).

Base materials for the non-heating volatile formulations include, for example, thermoplastic resins, filter papers and Japanese papers.

The base material for poisonous bait includes, for example, bait components (e.g., cereal flour, vegetable oils, saccharides and crystalline cellulose), antioxidants (e.g., dibutylhydroxytoluene and nordihydroguaiaretic acid), preservatives (e.g., dehydroacetic acid), agents for preventing consumption by children or pets (e.g., red pepper powder) and attractants (e.g., cheese perfume, onion perfume and peanut oil).

The flowable concentrates (aqueous suspension concentrates or aqueous emulsion concentrates) usually contain the present compound, a dispersant, a suspension assistant (e.g., a protective colloid or a compound capable of imparting thixotropic properties), suitable auxiliaries (e.g., defoaming agents, rust preventives, stabilizers, spreaders, penetration assistants, antifreezing agents, bactericides and fungicides) and water. The protective colloid includes, for example, gelatin, casein, gums, cellulose ether and poly(vinyl alcohol) s. The compound capable of imparting thixotropic properties includes, for example, bentonite, aluminum magnesium silicate, xanthan gum and poly(acrylic acid)s. It is also possible to prepare an oil-based suspension concentrate by using, in place of water, an oil substantially incapable of dissolving the present compound.

It is also possible to apply the present compound in admixture or combination with other insecticides, acaricides, repellents, synergists or the like.

The active ingredients of the insecticides and acaricides include, for example, organophosphorus compounds such as Fenitrothion [O,O-dimethyl O-(3-methyl-4-nitrophenyl) phosphorothioate], Fenthion [O,O-dimethyl O-(3-methyl-4-(methylthio)phenyl)phos-phorothioate], Diazinon [O,O-diethyl O-2-isopropyl-6-methylpyrimidin-4-yl phosphorothioate], Chlorpyrifos [O,O-diethyl O-3,5,6-trichloro-2-pyridyl phosphorothioate], Acephate [O,S-dimethyl acetylphosphoramidothioate], Methidathion [S-2,3-dihydro-5-methoxy-2-oxo-1,3,4-thiadiazol-3-ylmethyl O,O-dimethylphosphorodithioate], Disulfoton [O,O-diethyl S-2-ethylthioethylphosphorodithioate], DDVP [2,2-dichlorovinyl dimethyl phosphate], Sulprofos [O-ethyl O-4-(methylthio)phenyl S-propyl phosphorodithioate], Cyanophos [O-4-cyanophenyl O,O-dimethyl phosphorothioate], Dioxabenzophos [2-methoxy-4H-1,3,2-benzodioxaphosphorine-2-sulfide], Dimethoate [O,O-dimethyl-S-(N-methylcarbamoylmethyl) dithiophosphate], Phenthoate [ethyl 2-dimethoxyphosphinothioylthio-(phenyl)acetate], Malathion [diethyl (dimethoxyphosphinothioylthio)succinate], Trichlorfon [dimethyl 2,2,2,-trichloro-1-hydroxyethylphosphonate], Azinphosmethyl [S-3,4-dihydro-4-oxo-1,2,3-benzotriazin-3-ylmethyl O,O-dimethylphosphorodithioate], Monocrotophos [dimethyl (E)-1-methyl-2-(methylcarbamoyl) vinylphosphate] and Ethion [O,O,O',O'-tetraethyl S,S'-methylenebis(phosphorodithioate)]; carbamate compounds such as BPMC [2-sec-butylphenyl methylcarbamate], Benfuracarb [ethyl N-[2,3-dihydro-2,2-dimethylbenzofuran-7-yloxycarbonyl(methyl)aminothio]-N-isopropyl-β-alaninate], Propoxur [2-isopropoxyphenyl N-methylcarbamate], Carbosulfan [2,3-dihydro-2,2-dimethyl-7-benzo[b]furanyl N-dibutylaminothio-N-methylcarbamate], Carbaryl [1-naphthyl N-methylcarbamate], Methomyl [S-methyl-N-[(methylcarbamoyl)oxy] thioacetimidate], Ethiofencarb [2-(ethylthiomethyl)phenyl methylcarbamate], Aldicarb [2-methyl-2-(methylthio)propionaldehyde O-methycarbamoyloxime], Oxamyl [N,N-dimethyl-2-methylcarbamoyloxyimino-2-(methylthio)acetamide] and Fenothiocarb [(S-4-phenoxybutyl)-N,N-dimethylthiocarbamate]; pyrethroid compounds such as Etofenprox [2-(4-ethoxyphenyl)-2-methylpropyl-3-phenoxybenzyl ether], Fenvalerate [(RS)-α-cyano-3-phenoxybenzyl (RS)-2-(4-chlorophenyl)-3-methylbutyrate], Esfenvalerate [(S)-β-cyano-3-phenoxybenzyl (S)-2-(4-chlorophenyl)-3-methylbutyrate], Fenpropathrin [(RS)-α-cyano-3-phenoxybenzyl 2,2,3,3-tetramethylcyclopropanecarboxylate], Cypermethrin [(RS)-α-cyano-3-phenoxybenzyl (1RS)-cis,trans-3-(2,2-dichlorovinyl)-2,2-dimethylcyclopropanecarboxylate], Permethrin [3-phenoxybenzyl (1RS)-cis,trans-3-(2,2-dichlorovinyl)-2,2-dimethylcyclopropanecarboxylate], Cyhalothrin [(RS)-α-cyano-3-phenoxybenzyl (Z)-(1RS)-cis-3-(2-chloro-3,3,3-trifluoroprop-1-enyl)-2,2-dimethylcyclopropanecarboxylate], Deltamethrin [(S)-α-cyano-3-phenoxybenzyl (1R)-cis-3-(2,2-dibromovinyl)-2,2-dimethylcyclopropanecarboxylate], Cycloprothrin [(RS)-α-cyano-3-phenoxybenzyl (RS)-2,2-dichloro-1-(4-ethoxyphenyl)cyclopropanecarboxylate], Fluvalinate [α-cyano-3-phenoxybenzyl N-(2-chloro-α, α, α-trifluoro-p-tolyl)-D-valinate], Bifenthrin [(2-methylbiphenyl-3-ylmethyl)(Z)-(1RS)-cis-3-(2-chloro-3,3,3-trifluoroprop-1-enyl)-2,2-dimethylcyclopropanecarboxylate], 2-methyl-2-(4-bromodifluoromethoxyphenyl)propyl (3-phenoxybenzyl) ether, Tralomethrin [(S)-α-cyano-3-phenoxybenzyl (1R-cis)-3-{(1RS)-(i,2,2,2-tetrabromoethyl)}-2,2-dimethylcyclopropanecarboxylate], Silafluofen [4-ethoxyphenyl{3-(4-fluoro-3-phenoxyphenyl)propyl}-dimethylsilane], d-Phenothrin [3-phenoxybenzyl (1R-cis,trans)-chrysanthemate], Cyphenothrin [(RS)-α-cyano-3-phenoxybenzyl (1R-cis,trans)-chrysanthemate], d-Resmethrin [5-benzyl-3-furylmethyl (1R-cis,trans)-chrysanthemate], Acrinathrin [(S)-α-cyano-3-phenoxybenzyl (1R-cis(Z))-(2,2-dimethyl-3-{3-oxo-3-(1,1,1,3,3,3-hexafluoropropyloxy)propenyl}-cyclopropanecarboxylate], Cyfluthrin [(RS)-α-cyano-4-fluoro-3-phenoxybenzyl 3-(2,2-dichlorovinyl)-2,2-dimethylcyclopropanecarboxylate], Tefluthrin [2,3,5,6-tetrafluoro-4-methylbenzyl (1RS-cis(Z))-3-(2-chloro-3,3,3-trifluoroprop-1-enyl)-2,2-dimethylcyclopropanecarboxylate], Transfluthrin [2,3,5,6-tetrafluorobenzyl (1R-trans)-3-(2,2-dichlorovinyl)-2,2-dimethylcyclopropanecarboxylate], Tetramethrin [3,4,5,6-tetrahydrophthalimidomethyl (1RS)-cis,trans-chrysanthemate], Allethrin [(RS)-3-allyl-2-methyl-4-oxocyclopent-2-enyl (1RS)-cis,trans-chrysanthemate], Prallethrin [(S)-2-methyl-4-oxo-3-(2-propynyl)cyclopent-2-enyl (1R)-cis,trans-chrysanthemate], Empenthrin [(RS)-1-ethynyl-2-methyl-2-pentenyl (1R)-cis,trans-chrysanthemate], Imiprothrin [2,5-dioxo-3-(prop-2-ynyl)imidazolidin-1-ylmethyl (1R)-cis,trans-2,2-dimethyl-3-(2-methylprop-1-enyl)cyclopropane-carboxylate], d-Furamethrin [5-(2-propynyl)furfuryl (1R)-cis,trans--chrysanthemate] and 5-(2-propynyl)-furfuryl 2,2,3,3-tetramethylcyclopropanecarboxylate]; nitroimidazolidine derivatives; N-cyanoamidine derivatives such as N-cyano-N'-methyl-N'-(6-chloro-3-pyridylmethyl)acetoamidine; chlorinated hydrocarbon compounds such as Endosulfan [6,7,8,9,10,10-hexachloro-1,5,5a,6,9,9a-hexahydro-6,9-methano-2,4,3-benzodioxathiepin oxide], γ-BHC [1,2,3,4,5,6-hexachlorocyclohexane] and 1,1-bis(chlorophenyl)-2,2,2-trichloroethanol; benzoylphenylurea compounds such as Chlorfluazuron [1-(3,5-dichloro-4-(3-chloro-5-trifluoromethylpyridin-2-yloxy)phenyl)-3-(2,6-difluorobenzoyl)urea], Teflubenzuron [1-(3,5-dichloro-2,4-difluorophenyl)-3-(2,6-difluorobenzoyl)urea] and Flufenoxuron [1-[4-(2-chloro-4-trifluoromethylphenoxy)-2-fluorophenyl]-3-(2,6-difluorobenzoyl)urea]; thiourea derivatives such as Diafenthiuron [N-(2,6-diisopropyl-4-phenoxyphenyl)-N'-tert-butylcarbodiimide]; phenylpyrazole compounds; Metoxadiazon [5-methoxy-3-(2-methoxyphenyl)-1,3,4-oxadiazol-2-(3H)-one], Bromopropylate [isopropyl 4,4'-dibromobenzilate], Tetradifon [4-chlorophenyl 2,4,5-trichlorophenyl-sulfone], Quinomethionate [S,S-6-methylquinoxaline-2,3-diyldithiocarbonate], Pyridaben [2-tert-butyl-5-(4-tert-butylbenzylthio)-4-chloropyridazin-3(2H)-one], Fenpyroximate [tert-butyl(E)-4-[(1,3-dimethyl-5-phenoxypyrazol-4-yl)methyleneaminooxymethyl] benzoate], Tebufenpyrad [N-4-tert-butylbenzyl)-4-chloro-3-ethyl-1-methyl-5-pyrazolecarboxamide], Polynactin complexes [tetranactin, dinactin and trinactin], Pyrimidifen [5-chloro-N-[2-{4-(2-ethoxyethyl)-2,3-dimethylphenoxy}-ethyl]-6-ethylpyrimidine-4-amine], Milbemectin, Abamectin, ivermectin, azadirachtin [AZAD], etc.

The repellents include, for example, 3,4-caranediol, N,N-diethyl-m-toluamide, 1-methylpropyl 2-(2-hydroxyethyl)-1-piperidinecarboxylate, p-menthane-3,8-diol, and plant essential oils such as hyssop oil.

The synergists include, for example, bis-(2,3,3,3-tetrachloropropyl) ether (S-421), N-(2-ethylhexyl)bicyclo[2.2.1]hept-5-ene-2,3-dicarboximide (MGK-264), and α-[2-(2-butoxyethoxy)ethoxy]-4,5-methylenedioxy-2-propyltoluene (piperonyl butoxide).

When the present compound is used as an active ingredient of a composition for controlling pest, formulations in the form of emulsifiable concentrates, wettable powders or flowable concentrates are applied usually after having been diluted with water so that the formulations have a concentration of the present compound falling within the range of from 0.1 to 10,000 ppm. Formulations in the form of oil formulations, aerosols, fumigrants, smoking formulations, volatile formulations, foggings, ULV formulations, poisonous baits or resin formulations are applied as they are.

Both the applying dosage and the applying concentration of the above formulations can be properly determined depending on conditions such as the type of formulations, when, where and how these formulations are applied, kind of pests, degree of damage, and the like.

The present compound exhibits a marked controlling effect (insecticidal, knocking-down and repellent effect) when vaporized by heating. Therefore, it is particularly useful as an active ingredient of a composition for controlling pest for preventing domestic epidemics.

The present invention is illustrated with reference to the following production example, formulation examples and test examples, which should not be construed as limiting the scope of the invention.

Firstly, production of the present compound is exemplified.

PRODUCTION EXAMPLE 1

0.90 Gram of 3-(2-methyl-1-propenyl)-2,2-dimethylcyclopropanecarboxylic acid chloride {containing the stereoisomers in a ratio of (1R)-trans form: (1R)-cis form: (1S)-trans form: (1S)-cis form=93.9:2.5:3.5:0.1} was added to a mixture of 1.0 g of 4-methoxymethyl-2,3,5,6-tetrafluorobenzyl alcohol, 0.42 g of pyridine and 10 ml of tetrahydrofuran under ice-cooling. The resulting mixture was heated to room temperature and stirred at room temperature for 8 hours. The reaction mixture was poured into about 50 ml of ice water and extracted twice with 80 ml of ethyl acetate. The combined ethyl acetate layer was washed with a saturated aqueous sodium chloride solution, dried over anhydrous sodium sulfate and then concentrated under reduced pressure. The resultant residue was subjected to silica gel column chromatography to obtain 1.40 g (yield: 84%) of 4-methoxymethyl-2,3,5,6-tetrafluorobenzyl 3-(2-methyl-1-propenyl)-2,2-dimethylcyclopropanecarboxylate (hereinafter referred to as the present compound 1).

$^1$H-NMR (CDCl$_3$, TMS internal standard) δ values (ppm): 1.13(s, 3H), 1.26(s, 3H), 1.38(d, 1H), 1.69(brs, 6H), 2.10(dd, 1H), 3.40(s, 3H), 4.59(s, 2H), 4.87(d, 1H), 5.24(dd, 2H).

PRODUCTION EXAMPLE 2

0.50 Gram of 3-(2-methyl-1-propenyl)-2,2-dimethylcyclopropanecarboxylic acid chloride {containing the stereoisomers in a ratio of (1R)-trans form: (1R)-cis form: (1S)-trans form: (1S)-cis form =32.5:17.5:32.5:17.5} was added to a mixture of 0.55 g of 4-methoxymethyl-2,3,5,6-tetrafluorobenzyl alcohol, 0.23 g of pyridine and 7 ml of tetrahydrofuran under ice-cooling. The resulting mixture was heated to room temperature and stirred at room temperature for 8 hours. The reaction mixture was poured into about 20 ml of ice water and extracted twice with 40 ml of ethyl acetate. The combined ethyl acetate layer was washed with a saturated aqueous sodium chloride solution, dried over anhydrous sodium sulfate and then concentrated under reduced pressure. The resultant residue was subjected to silica gel column chromatography to obtain 0.74 g (yield: 80%) of 4-methoxymethyl-2,3,5,6-tetrafluorobenzyl 3-(2-methyl-1-propenyl)-2,2-dimethylcyclopropanecarboxylate (hereinafter referred to as the present compound 2).

$^1$H-NMR (CDCl$_3$, TMS internal standard) δ values (ppm): 1.13 and 1.19(s, 3H in total), 1.24 and 1.26(s, 3H in total), 1.38 and 1.67(d, 1H in total), 1.68(brs, 6H), 1.90 and 2.08(dd, 1H in total), 3.40(s, 3H), 4.59(s, 2H), 4.88 and 5.17(d, 1H in total), 5.23(dd, 2H).

PRODUCTION EXAMPLE 3

3-(2-methyl-1-propenyl)-2,2-dimethylcyclopropanecarboxylic acid chloride {containing the stereoisomers in a ratio of (1R)-trans form (1R)-cis form: (1S)-trans form: (1S)-cis form=49:1:49:1} is added to a mixture of 4-methoxymethyl-2,3,5,6-tetrafluorobenzyl alcohol, pyridine and tetrahydrofuran under ice-cooling. The resulting mixture is heated to room temperature and stirred at room temperature. The reaction mixture is poured into ice water and extracted with ethyl acetate. The combined ethyl acetate layer is washed with a saturated aqueous sodium chloride solution, dried over anhydrous sodium sulfate and then concentrated under reduced pressure. The resultant residue is subjected to silica gel column chromatography to obtain 4-methoxymethyl-2,3,5,6-tetrafluorobenzyl 3-(2-methyl-1-propenyl)-2,2-dimethylcyclopropane-carboxylate (hereinafter referred to as the present compound 3).

PRODUCTION EXAMPLE 4

3-(2-methyl-1-propenyl)-2,2-dimethylcyclopropanecarboxylic acid chloride {containing the stereoisomers in a ratio of (1R)-trans form: (1R)-cis form: (1S)-trans form: (1S)-cis form=25:25:25:25} is added to a mixture of 4-methoxymethyl-2,3,5,6-tetrafluorobenzyl alcohol, pyridine and toluene under ice-cooling. The resulting mixture is heated to room temperature and stirred at room temperature. The reaction mixture is poured into ice water to be separated. The organic layer thus separated is washed with a 15% aqueous sodium chloride solution, dried over anhydrous sodium sulfate and then concentrated under reduced pressure. The resultant residue is subjected to silica gel column chromatography to obtain 4-methoxymethyl-2,3,5,6-tetrafluorobenzyl 3-(2-methyl-1-propenyl)-2,2-dimethylcyclopropanecarboxylate (hereinafter referred to as the present compound 4).

PRODUCTION EXAMPLE 5

1-(3-dimethylaminopropyl)-3-ethylcarbodiimide hydrochloride is added to a mixture of 4-methoxymethyl-2,3,5,6-tetrafluorobenzyl alcohol, 3-(2-methyl-1 -propenyl)-2,2-dimethylcyclopropanecarboxylic acid {containing the stereoisomers in a ratio of (1R)-trans form: (1R)-cis form: (1S)-trans form: (1S)-cis form=99:0:1:0} and tetrahydrofuran under ice-cooling. The resulting mixture is heated to room temperature and stirred at room temperature. The reaction mixture is poured into ice water and extracted with ethyl acetate. The combined ethyl acetate layer is washed with a saturated aqueous sodium chloride solution, dried over anhydrous sodium sulfate and then concentrated under reduced pressure. The resultant residue is subjected to silica gel column chromatography to obtain 4-methoxymethyl-2,3,5,6-tetrafluorobenzyl 3-(2-methyl-1-propenyl)-2,2-dimethylcyclopropanecarboxylate (hereinafter referred to as the present compound 5).

PRODUCTION EXAMPLE 6

1- (3-dimethylaminopropyl) -3-ethylcarbodiimide hydrochloride is added to a mixture of 4-methoxymethyl-2,3,5,6-tetrafluorobenzyl alcohol, 3- (2-methyl-1-propenyl) -2,2-dimethylcyclopropanecarboxylic acid {containing the stereoisomers in a ratio of (1R)-trans form: (1R)-cis form: (1S)-trans form: (1S)-cis form=49:49:1:1} and toluene under ice-cooling. The resulting mixture is heated to room temperature and stirred at room temperature. The reaction mixture is poured into ice water to be separated. The organic layer thus separated is washed with a saturated aqueous sodium chloride solution, dried over anhydrous sodium sulfate and then concentrated under reduced pressure. The resultant residue is subjected to silica gel column chromatography to obtain 4-methoxymethyl-2,3,5,6-tetrafluorobenzyl 3-(2-methyl-1-propenyl)-2,2-dimethylcyclopropanecarboxylate (hereinafter referred to as the present compound 6).

PRODUCTION EXAMPLE 7

3-(2-methyl-1-propenyl)-2,2-dimethylcyclopropanecarboxylic acid chloride {containing the stereoisomers in a ratio of (1R)-trans form: (1R)-cis form: (1S)-trans form: (1S)-cis form=76:19:4:1} is added to a mixture of 4-methoxymethyl-2,3,5,6-tetrafluorobenzyl alcohol, pyridine and tetrahydrofuran under ice-cooling. The resulting mixture is heated to room temperature and stirred at room temperature. The reaction mixture is poured into ice water and extracted with ethyl acetate. The combined ethyl acetate layer is washed with a saturated aqueous sodium chloride solution, dried over anhydrous sodium sulfate and then concentrated under reduced pressure. The resultant residue is subjected to silica gel column chromatography to obtain 4-methoxymethyl-2,3,5,6-tetrafluorobenzyl 3-(2-methyl-1-propenyl)-2,2-dimethylcyclopropane-carboxylate (hereinafter referred to as the present compound 7).

Next, formulation examples are described below. In the formulation examples, parts are all by weight.

FORMULATION EXAMPLE 1

20% Emulsifiable concentrates of each of the present compounds 1 to 7 are obtained by dissolving 20 parts of each of the present compounds in 65 parts of xylene, and adding thereto 15 parts of an emulsifier Sorpol 3005X (a registered trade name, Toho Chemical Co., Ltd.), and thoroughly stirring and mixing the resulting mixture.

FORMULATION EXAMPLE 2

40% Wettable powders of each of the present compounds 1 to 7 are obtained by thoroughly mixing 40 parts of each of the present compounds with 5 parts of Sorpol 3005X (described above), adding thereto 32 parts of Carplex #80 (a registered trade name, Shionogi & Co., Ltd.; fine powder of synthetic hydrated silicon dioxide) and 23 parts of 300-mesh diatomaceous earth, and stirring and mixing the resulting mixture in a juice mixer.

FORMULATION EXAMPLE 3

1.5% Granules of each of the present compounds 1 to 7 are obtained by thoroughly mixing 1.5 parts of each of the present compounds with 98.5 parts of AGSORBLVM-MS 24/48 (a calcined product of montmorillonite, a granular carrier with a particle size of 24 to 48 mesh, mfd. by OIL DRI Corp.).

FORMULATION EXAMPLE 4

A mixture of 10 parts of each of the present compounds 1 to 7, 10 parts of phenylxylylethane and 0.5 part of Sumidur L-75 (tolylene diisocyanate, mfd. by Sumitomo Bayer Urethane Co. Ltd.) is added to 20 parts of a 10% aqueous gum arabic solution. The resulting mixture is stirred in a homomixer to obtain an emulsion having an average particle size of 20 μm. Then, 2 parts of ethylene glycol is added to the emulsion. The resultant mixture is allowed to react on a hot bath at 60° C. for 24 hours to obtain a microcapsule slurry. On the other hand, 0.2 part of xanthan gum and 1.0 part of Veegum R (aluminum magnesium silicate, mfd. by Sanyo Chemical Industries Ltd.) are dispersed in 56.3 parts of ion-exchanged water to obtain a thickening agent solution.

42.5 Parts of the microcapsule slurry prepared above and 57.5 parts of the thickening agent solution prepared above are mixed to obtain 10% microcapsules.

FORMULATION EXAMPLE 5

A mixture of 10 parts of each of the present compounds 1 to 7 and 10 parts of phenylxylylethane is added to 20 parts of a 10% poly(ethylene glycol) aqueous solution. The resulting mixture is stirred in a homomixer to obtain an emulsion having an average particle size of 3 μm. On the other hand, 0.2 part of xanthan gum and 1.0 part of Veegum R (aluminum magnesium silicate, mfd. by Sanyo Chemical Industries Ltd.) are dispersed in 58.8 parts of ion-exchanged water to obtain a thickening agent solution.

40 Parts of the emulsion prepared above and 60 parts of the thickening agent solution prepared above are mixed to obtain a 10% flowable concentrate.

FORMULATION EXAMPLE 6

5% Dusts of each of the present compounds 1 to 7 are obtained by stirring and mixing 5 parts of each of the present compounds, 3 parts of Carplex #80 (a registered trade name, Shionogi & Co., Ltd.; fine powder of synthetic hydrated silicon dioxide), 0.3 part of PAP and 91.7 parts of 300-mesh talc in a juice mixer.

FORMULATION EXAMPLE 7

0.1% Oil formulations of each of the present compounds 1 to 7 are obtained by dissolving 0.1 part of each of the present compounds in 5 parts of dichloro-methane and mixing the resulting solution with 94.9 parts of deodorized kerosene.

FORMULATION EXAMPLE 8

Oil-based aerosols of each of the present compounds 1 to 7 are obtained by mixing 1 part of each of the present compounds, 5 parts of dichloromethane and 34 parts of deodorized kerosene to obtain a solution, charging the solution into an aerosol container, attaching a valve part to the container, and then compressing 60 parts of a propellant (liquefied petroleum gas) into the container under pressure through the valve part.

FORMULATION EXAMPLE 9

Water-based aerosols of each of the present compounds 1 to 7 are obtained by mixing 0.6 part of each of the present compounds, 5 parts of xylene, 3.4 parts of deodorized kerosene and 1 part of an emulsifier (Atmos 300 (a registered trade name, Atlas Chemical Corp.)) to obtain a solution, charging the solution together with 50 parts of pure water into an aerosol container, attaching a valve part to the container, and then compressing 40 parts of a propellant (liquefied petroleum gas) into the container under pressure through the valve part.

FORMULATION EXAMPLE 10

Mosquito coils of each of the present compounds 1 to 7 are obtained by dissolving 0.3 g of each of the present compounds in 20 ml of acetone, stirring and mixing uniformly the resulting solution with 99.7 g of a carrier for insecticidal coil (a mixture of Tabu powder, Pyrethrum marc and wood powder in the ratio of 4:3:3), adding thereto 120 ml of water, thoroughly kneading the resulting mixture, and molding and drying the kneaded mixture.

FORMULATION EXAMPLE 11

Acetone is added to a mixture of 0.8 g of each of the present compounds 1 to 7 and 0.4 g of piperonyl butoxide to prepare a solution having a total volume of 10 ml. A base material for electric mat (a plate obtained by coagulating fibrils of a mixture of cotton linter and pulp) having an area of 2.5 cm×1.5 cm and a thickness of 0.3 cm is uniformly impregnated with 0.5 ml of the solution prepared above, to obtain electric insecticidal mats containing each of the present compounds.

FORMULATION EXAMPLE 12

Parts used for an absorbent-wick type heating vaporization device containing each of the present compounds are obtained by dissolving 3 parts of each of the present compounds 1 to 7 in 97 parts of deodorized kerosene to obtain a solution, placing the solution in a container made of vinyl chloride, and inserting one end of an absorbent wick (obtained by coagulating inorganic powder with a binder and baking the coagulated powder) into the container so that the other end of the wick can be heated with a heater.

FORMULATION EXAMPLE 13

Heating smoking formulations of each of the present compounds 1 to 7 are obtained by dissolving 100 mg of each of the present compounds in an adequate amount of acetone to obtain a solution, and impregnating a porous ceramic plate having an area of 4.0 cm square and a thickness of 1.2 mm with the solution.

FORMULATION EXAMPLE 14

Non-heating volatile formulations of each of the present compounds 1 to 7 are obtained by dissolving 100 μg of each of the present compounds in an adequate amount of acetone, applying the resulting solution uniformly on a filter paper having an area of 2 cm square and a thickness of 0.3 mm, and then air-drying the filter paper to remove the acetone.

FORMULATION EXAMPLE 15

Acarine-controlling sheets of each of the present compounds 1 to 7 are obtained by impregnating a filter paper with a solution of each of the present compounds in acetone so that the filter paper contains each of the present compounds in a concentration of 1 gram per square meter, and air-drying the filter paper to remove the acetone.

TEST EXAMPLE 1

A base material for insecticidal coil was prepared by stirring a 4:3:3 mixture of Tabu powder, Pyrethrum marc and wood powder, adding water thereto, thoroughly kneading the resulting mixture, and molding and drying the kneaded mixture. The base material was uniformly impregnated with a solution of the present compound 1 in acetone so that the material contains a predetermined amount of the present compound 1. The resultant base material was air-dried to obtain an insecticidal coil.

Four nylon cages were prepared by covering a cylindrical iron frame having a diameter of 20 cm and a height of 20 cm with a 16-mesh net. Twenty female adult common mosquitoes (*Culex pipiens pallens*) were released in each of the four nylon cages. The four nylon cages were suspended in a test chamber (2.65 m×4.3 m×2.45 m (height)) at a horizontal distance of 60 cm from the center of the chamber in 4 directions, respectively, in relation to the center of the chamber so that the bottom of each cage might be kept at a height of 60 cm above the floor of the chamber. An electric fan was placed in the center of the chamber. An iron plate was placed on the electric fan. An insecticidal coil containing the present compound 1 was set on a holder, and the holder was placed on the iron plate. The coil was ignited at one end thereof. During the test, the coil was allowed to continue burning. The air in the chamber was agitated with the electric fan. The knocked-down common mosquitoes were counted in 15 minutes and 20 minutes after the ignition of the coil. In 60 minutes after the ignition of the coil, the test insects were collected in a cup for recovery and given water and diet. The dead and alive were counted in 24 hours.

The same test as above was repeated while replacing the present compound 1 with, as the reference compound, 4-methoxymethyl-2,3,5,6-tetrafluorobenzyl 3-(2,2-dichlorovinyl)-2,2-dimethylcyclopropanecarboxylate (hereinafter referred to as the reference compound 1). The reference compound 1 was prepared from 4-methoxymethyl-2,3,5,6-tetrafluorobenzyl alcohol and 3-(2,2-dichlorovinyl)-2,2-dimethylcyclopropanecarboxylic acid {containing the stereoisomers in a ratio of (1R)-trans form: (1R)-cis form: (1S)-trans form: (1S)-cis form= 99.4:0.0:0.6:0.0} according to the process disclosed in EP-A-54360.

Table 1 shows the results.

TABLE 1

| Test compound | Concentration % w/w | Number of normal insects (insects not knocked down) [of 80 insects] | | Number of surviving insects [of 80 insects] |
| --- | --- | --- | --- | --- |
| | | In 15 min. | In 20 min. | |
| Present compound 1 | 0.05 | 21 | 1 | 1 |
| Reference compound 1 | 0.05 | 55 | 26 | 13 |

TEST EXAMPLE 2

A base material for insecticidal coil was prepared by stirring a 4:3:3 mixture of Tabu powder, Pyrethrum marc and wood powder, adding water thereto, thoroughly kneading the resulting mixture, and molding and drying the kneaded mixture. The base material was uniformly impregnated with a solution of the present compound 2 in acetone so that the material contains a predetermined amount of the present compound 2. The resultant base material was air-dried to obtain an insecticidal coil. 0.5 Gram of the insecticidal coil containing the present compound 2 prepared according to the procedure described above was set on a holder. The holder was placed in the center of the bottom of a glass chamber (70 cm cube, capacity: 0.34 cm3) . The coil was ignited at one end thereof. After completion of the combustion of the coil, 20 female adult common mosquitoes (*Culex pipiens pallens*) were released in the chamber. In 5 minutes, the knocked-down common mosquitoes were counted. The test was carried out in duplicate.

The same test as above was repeated while replacing the present compound 2 with, as the reference compound, 4-methoxymethyl-2,3,5,6-tetrafluorobenzyl 3-(2,2-dichlorovinyl)-2,2-dimethylcyclopropanecarboxylate (hereinafter referred to as the reference compound 2). The reference compound 2 was prepared from 4-methoxymethyl-2,3,5,6-tetrafluorobenzyl alcohol and 3-(2,2-dichlorovinyl)-2,2-dimethylcyclopropanecarboxylic acid {containing the stereoisomers in a ratio of (1R)-trans form (1R)-cis form (1S)-trans form: (1S)-cis form=28.0 22.0:28.0:22.0} according to the process disclosed in EP-A-54360.

Table 2 shows the results.

TABLE 2

| Test compound | Concentration % w/w | Number of normal insects (insects not knocked down) [of 40 insects] |
| --- | --- | --- |
| Present compound 2 | 0.1 | 1 |
| Reference compound 2 | 0.1 | 11 |

As is clear from the results, the present compounds have unexpectedly higher knocking-down activity and insecticidal activity than do the reference compounds. Thus, they are useful as an active ingredient of compositions for controlling pest.

The present compounds are excellent in pest-controlling effect and are very useful as an active ingredient of compositions for controlling pest, in particular, compositions for controlling pest for preventing domestic epidemics.

What is claimed is:

1. 4-methoxymethyl-2,3,5,6-tetrafluorobenzyl 3-(2-methyl-1-propenyl)-2,2-dimethylcyclopropanecarboxylate represented by the formula:

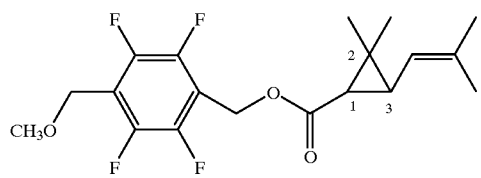

2. The compound according to claim 1, wherein the cyclopropane ring has R-configuration in 1-position.

3. The compound according to claim 2, wherein the substituent in 1-position of the cyclopropane ring has trans-configuration relative to the substituent in 3-position of the cyclopropane ring.

4. A composition for controlling pest, which comprises a compound according to claim 1 as an active ingredient and a carrier.

5. A method for controlling pests, which comprises applying an effective amount of a compound according to claim 1 to the pests or a locus where the pests inhabit.

* * * * *